United States Patent
Liu et al.

(10) Patent No.: US 10,693,107 B2
(45) Date of Patent: Jun. 23, 2020

(54) ORGANIC ELECTROLUMINESCENCE DEVICE HAVING RGB PIXEL AREAS

(71) Applicants: BEIJING VISIONOX TECHNOLOGY CO., LTD., Shangdi, Haidian District Beijing (CN); KUNSHAN NEW FLAT PANEL DISPLAY TECHNOLOGY CENTER CO., LTD., Development Zone KunShan, Jiansu (CN); KUNSHAN GO-VISIONOX OPTO-ELECTRONICS CO., LTD., Development Zone KunShan, Jiansu (CN)

(72) Inventors: Song Liu, Beijing (CN); Weiwei Li, Beijing (CN); Lin He, Beijing (CN)

(73) Assignees: BEIJING VISIONOX TECHNOLOGY CO., LTD., Shanghai, Haidian (CN); KUNSHAN NEW FLAT PANEL DISPLAY TECHNOLOGY CENTER CO., LTD., Development Zone (CN); KUNSHAN GO-VISIONOX OPTO-ELECTRONICS CO., LTD., Development Zone (CN)

(*) Notice: Subject to any disclaimer, the term of this patent is extended or adjusted under 35 U.S.C. 154(b) by 344 days.

(21) Appl. No.: 15/540,240

(22) PCT Filed: Dec. 29, 2015

(86) PCT No.: PCT/CN2015/099376
§ 371 (c)(1),
(2) Date: Jun. 27, 2017

(87) PCT Pub. No.: WO2016/107537
PCT Pub. Date: Jul. 7, 2016

(65) Prior Publication Data
US 2017/0373276 A1    Dec. 28, 2017

(30) Foreign Application Priority Data
Dec. 31, 2014  (CN) .................. 2014 1 0853953

(51) Int. Cl.
*H01L 51/52* (2006.01)
*H01L 51/50* (2006.01)
(Continued)

(52) U.S. Cl.
CPC ........ *H01L 51/5262* (2013.01); *C07C 211/54* (2013.01); *C07C 211/58* (2013.01);
(Continued)

(58) Field of Classification Search
CPC ... C07C 211/54; C07C 211/58; C07C 211/61; C07D 487/04; H01L 2251/552;
(Continued)

(56) References Cited

U.S. PATENT DOCUMENTS

2002/0182439 A1* 12/2002 Tao .................. C07C 211/54
                                                        428/690
2003/0044639 A1   3/2003 Fukuda
(Continued)

FOREIGN PATENT DOCUMENTS

CN    1711001    12/2005
CN    1773744    5/2006
(Continued)

OTHER PUBLICATIONS

National Center for Biotechnology Information. PubChem Database. Indenofluorene, CID=53629810, https://pubchem.ncbi.nlm.nih.gov/compound/Indenofluorene (accessed on Dec. 5, 2019) (Year: 2019).*
(Continued)

*Primary Examiner* — Dawn L Garrett
(74) *Attorney, Agent, or Firm* — Kilpatrick Townsend & Stockton, LLP

(57) ABSTRACT

An organic electroluminescence device having RGB pixel areas, wherein optical compensation layers are respectively arranged between the red light emitting layer and the first
(Continued)

organic functional layer as well as between the green light emitting layer and the first organic functional layer, the optical compensation layers are made of a first hole transport material and a second hole transport material, the first hole transport material has a triplet-state energy level ≥2.48 eV and a HOMO energy level ≤−5.5 eV, the second hole transport material has a HOMO energy level >−5.5 eV, and the difference between the HOMO energy level of the first hole transport material and the HOMO energy level of the second hole transport material is ≤0.2 eV. Its preparation process is simple, and it can significantly reduce power consumption of the light-emitting device so as to increase light-emitting efficiency.

8 Claims, 2 Drawing Sheets

(51) Int. Cl.
  *H01L 27/32* (2006.01)
  *H01L 51/00* (2006.01)
  *C07C 211/54* (2006.01)
  *C07C 211/58* (2006.01)
  *C07C 211/61* (2006.01)
  *C07D 487/04* (2006.01)

(52) U.S. Cl.
  CPC .......... *C07C 211/61* (2013.01); *C07D 487/04* (2013.01); *H01L 27/3211* (2013.01); *H01L 51/5004* (2013.01); *H01L 51/506* (2013.01); *H01L 51/5008* (2013.01); *H01L 51/5064* (2013.01); *H01L 51/5265* (2013.01); *H01L 51/006* (2013.01); *H01L 51/0052* (2013.01); *H01L 51/0054* (2013.01); *H01L 51/0055* (2013.01); *H01L 51/0058* (2013.01); *H01L 51/0059* (2013.01); *H01L 51/0067* (2013.01); *H01L 51/0071* (2013.01); *H01L 51/0072* (2013.01); *H01L 51/5056* (2013.01); *H01L 2251/552* (2013.01)

(58) Field of Classification Search
  CPC ............. H01L 27/3211; H01L 51/0052; H01L 51/0054; H01L 51/0055; H01L 51/0058; H01L 51/0059; H01L 51/006; H01L 51/0067; H01L 51/0071; H01L 51/0072; H01L 51/5004; H01L 51/5008; H01L 51/5056; H01L 51/506; H01L 51/5064; H01L 51/5262; H01L 51/5265
  See application file for complete search history.

(56) References Cited

U.S. PATENT DOCUMENTS

| | | | | |
|---|---|---|---|---|
| 2003/0162108 | A1* | 8/2003 | Burberry | ............ H01L 51/0009 430/20 |
| 2005/0280355 | A1 | 12/2005 | Lee et al. | |
| 2009/0079326 | A1 | 3/2009 | Seo et al. | |
| 2011/0266531 | A1* | 11/2011 | Kim | ....... H01L 51/005 257/40 |
| 2012/0161107 | A1* | 6/2012 | Yokoyama | ........... C07D 213/22 257/40 |
| 2012/0298968 | A1 | 11/2012 | Kim et al. | |
| 2012/0326141 | A1 | 12/2012 | Pflumm et al. | |
| 2013/0140530 | A1 | 6/2013 | Kho et al. | |
| 2013/0207046 | A1* | 8/2013 | Pflumm | ................ C07C 211/61 252/500 |
| 2013/0277656 | A1 | 10/2013 | Seo et al. | |
| 2013/0285036 | A1 | 10/2013 | Stoessel et al. | |
| 2014/0027732 | A1 | 1/2014 | Pyo et al. | |
| 2014/0239283 | A1* | 8/2014 | Kimura | ................ C07C 211/58 257/40 |
| 2014/0361257 | A1 | 12/2014 | Park et al. | |
| 2015/0041785 | A1* | 2/2015 | Sannomiya | .......... C07D 487/04 257/40 |

FOREIGN PATENT DOCUMENTS

| | | | |
|---|---|---|---|
| CN | 102110815 | | 6/2011 |
| CN | 102437290 | | 5/2012 |
| CN | 102675128 | A * | 9/2012 |
| CN | 102782084 | | 11/2012 |
| CN | 103137879 | | 6/2013 |
| CN | 103187537 | A | 7/2013 |
| CN | 103700776 | | 4/2014 |
| CN | 103904225 | | 7/2014 |
| CN | 104160525 | | 11/2014 |
| CN | 104241317 | | 12/2014 |
| CN | 104247076 | | 12/2014 |
| CN | 104538559 | | 4/2015 |
| JP | 2000323277 | A | 11/2000 |
| JP | 2013522864 | A | 6/2013 |
| KR | 20120100031 | | 9/2012 |
| KR | 20120130516 | | 12/2012 |
| TW | 201405907 | | 2/2014 |

OTHER PUBLICATIONS

Machine translation of CN 102675128 A (publication date: Sep. 2012). (Year: 2012).*
Transmittal regarding foreign literature, dated Nov. 9, 2018, 1 page.
JP First Office Action dated Mar. 14, 2019 in corresponding JP application (applicatiton No. 2017-535351).
EP Office Action dated Feb. 6, 2019 in the corresponding EP application (application No. 15875213.9).
Transmittal regarding foreign literature, dated Sep. 26, 2018, 1 page.
Supplementary European Search Report for the corresponding European Patent Application, EP15875213, dated Jul. 12, 2018, 10 pages.
Transmittal regarding foreign literature, dated Jul. 18, 2018, 2 pages.
International Search Report and Written Opinion with an English translation for corresponding PCT Application, PCT/CN2015/099376, including translation into English, dated Jun. 4, 2016, 16 pages.
Transmittal regarding foreign literature, dated Dec. 18, 2017, 2 pages.

* cited by examiner

ORGANIC ELECTROLUMINESCENCE DEVICE HAVING RGB PIXEL AREAS

TECHNICAL FIELD

The present invention pertains to the technical field of organic electroluminescence devices, and in particular relates to an organic electroluminescence device having optical compensation layers.

BACKGROUND

The light-emitting layer of an organic electroluminescence device OLED is mainly made of fluorescent material, or phosphorescent material, or mixed fluorescent and phosphorescent material. The LED display unit consists of three kinds of red, green, blue pixels, and when a top-emitting OLED device structure is used, because the three kinds of pixels have different light-emitting wavelengths, the thicknesses of the light-emitting layers would have certain differences. Usually, an optical compensation layer is utilized to modify the thickness of a light-emitting layer, the thickness of the optical compensation layer can be over 100 nm, so the optical compensation layer needs to have very good electrical charge transfer rate, in order to ensure that the device has the characteristics of low voltage and high efficiency.

The material used to make the existing optical compensation layer has a high triplet-state energy level, but often has low charge transfer rate and thus cannot be made to be thick enough, therefore, as an optical compensation layer, it has a high drive voltage. In another aspect, material with a high charge transfer rate often has a low triplet-state energy level, which adversely affects the efficiency of green-light devices. Currently, the optical compensation layer is arranged between HIL and HTL, and is made of material with a high hole transfer rate (1.5-2 times of the transfer rate of NPB), although such arrangement alleviates the thickness increase of the organic layer to a certain extent and does not adversely affect the drive voltage of the organic light-emitting device, it does not take the special electric characteristic requirements of different light-emitting material into consideration, and cannot effectively increase the efficiency of the organic light-emitting device and reduce the power consumption of the display device.

The patent literature CN201210395191.7 of Samsung discloses an electroluminescence device, as shown in FIG. 1, it sequentially comprises a substrate 110, a first electrode 120, a hole injection layer 130, a hole transport layer 140, a buffer layer 150, a light-emitting layer 160, an electron transport layer 170, an electron injection layer 180 and a second electrode 190. The hole transport layer 140 consists of sequentially deposited layers of a first charge generation layer 141, a first mixed layer 142, a second charge generation layer 143 and a second mixed layer 144. The first charge generation layer 141 can be made of a mixture that contains a first compound and a second compound and is doped with a first charge generation material; the first mixed layer 142 can be made of a mixture that contains the first compound and the second compound; the second charge generation layer 143 can be made of a mixture that contains a third compound and a fourth compound and is doped with a second charge generation material; the second mixed layer 144 can be made of a mixture that contains the third compound and the fourth compound, in this aspect, the third compound and the fourth compound has a weigh ratio of 6:4 to 8:2. In this patent, the charge generation layer cannot provide an effective function for blocking excitons, so the buffer layer is required.

The patent literature CN200510077967.0 discloses an electroluminescence device, as shown in FIG. 2, a second hole transport layer 18-2 is arranged upon a first hole transport layer 18-1 in a green-light pixel area 200; the second hole transport layer 18-2 and a third hole transport layer 18-3 are arranged upon the first hole transport layer 18-1 in a red-light pixel area 300. The first hole transport layer 18-1, the second hole transport layer 18-2 and the third hole transport layer 18-3 can be made of different materials, but these hole transport layers are made of the same material. Although this patent discloses utilization of hole transport layers with a mixed structure to increase light-emitting efficiency and such arrangement alleviates the thickness of the light-emitting layer to a certain extent, the HTL material suitable to make the green-light optical compensation layer is still required to have a high triplet-state energy level TI with its HOMO energy level ≤−5.5 eV, and this kind of material often has a low charge transfer rate and thus cannot be made to be thick enough, therefore, this device has a high drive voltage.

SUMMARY OF THE INVENTION

Accordingly, one objective of the present invention is to solve the technical problem that the red-light and green-light optical compensation layers in prior art are made of materials with a low charge transfer rate or a poor exciton blocking effect, by providing an organic electroluminescence device that has an optical compensation layer made of two hole transport materials with different energy gaps, which can significantly reduce power consumption of the light-emitting device, so as to increase light-emitting efficiency.

The present invention also provides a preparation method of the above-mentioned organic electroluminescence device.

In order to solve the above-mentioned technical problem, the present invention adopts the following technical scheme:

An organic electroluminescence device having RGB pixel areas comprises a substrate, with a first electrode layer, a plurality of organic layers and a second electrode layer formed in sequence on the substrate, wherein, the organic layers include a first organic functional layer, a light emitting layer and a second organic functional layer arranged upon the first electrode layer, the light emitting layer comprises a red light emitting layer, a green light emitting layer and a blue light emitting layer, wherein, optical compensation layers are respectively arranged between the red light emitting layer and the first organic functional layer as well as between the green light emitting layer and the first organic functional layer, the optical compensation layers are made of a first hole transport material and a second hole transport material, the first hole transport material has a triplet-state energy level ≥2.48 eV and a HOMO energy level ≤−5.5 eV, the second hole transport material has a HOMO energy level >−5.5 eV, and the difference between the HOMO energy level of the first hole transport material and the HOMO energy level of the second hole transport material is ≤0.2 eV.

The optical compensation layers include a red light optical compensation layer arranged between the red light emitting layer and the first organic functional layer, and a green light optical compensation layer arranged between the green light emitting layer and the first organic functional layer.

The first hole transport material and second hole transport material contained in the red light optical compensation layer has a mass ratio of 1:99 to 99:1.

The first hole transport material and second hole transport material contained in the green light optical compensation layer has a mass ratio of 5:95 to 50:50, preferably 10:90 to 30:70.

The first hole transport material has a structure defined by the following structural formula (1) or structural formula (2):

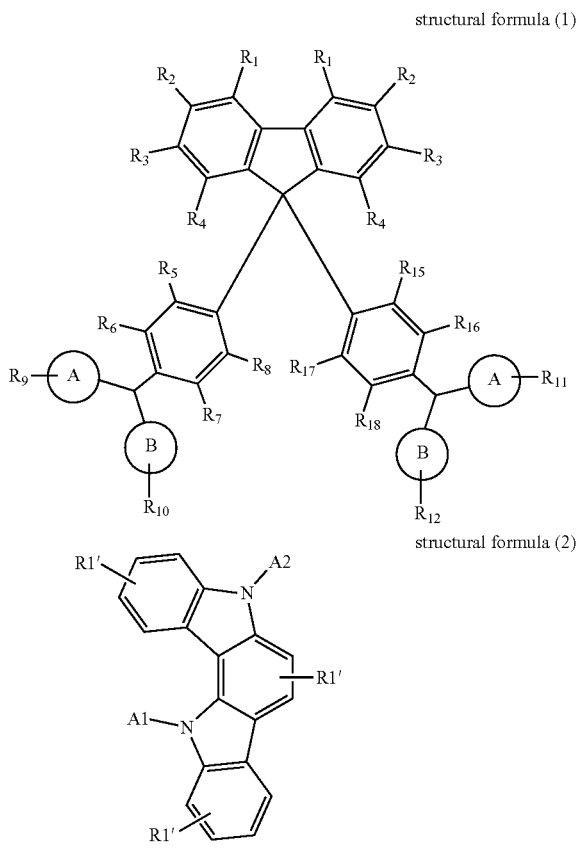

structural formula (1)

structural formula (2)

in the structural formula (1), the groups A and B are individually selected from phenyl group, naphthyl group or phenyl-amino group;
the groups of $R_1$, $R_2$, $R_3$, $R_4$, $R_5$, $R_6$, $R_7$, $R_8$, $R_{15}$, $R_{16}$, $R_{17}$ and $R_{18}$ are identical or different, and are individually selected from hydrogen element, halogen element, CN, $NO_2$, amino group, $C_6$-$C_{30}$ fused cyclic aryl group, $C_6$-$C_{30}$ fused heterocyclic aryl group, $C_6$-$C_{20}$ alkyl group or $C_6$-$C_{30}$ alcohol group;
the groups of $R_9$, $R_{10}$, $R_{11}$ and $R_{12}$ are identical or different, and are individually selected from $C_6$-$C_{30}$ aryl group;
in the structural formula (2), the groups of A1 and A2 are individually selected from $C_6$-$C_{30}$ aryl group or $C_6$-$C_{30}$ heterocyclic aryl group, the group R1' is selected from hydrogen, alkyl group, alkoxyl group or basic group;
and the structural formula (2) also meets the following condition: at least one of the groups of A1 and A2 has a condensed ring structure.

The first hole transport material has a structure selected from the following structural formulas (HTL1) to (HTL1-10):

HTL1-1

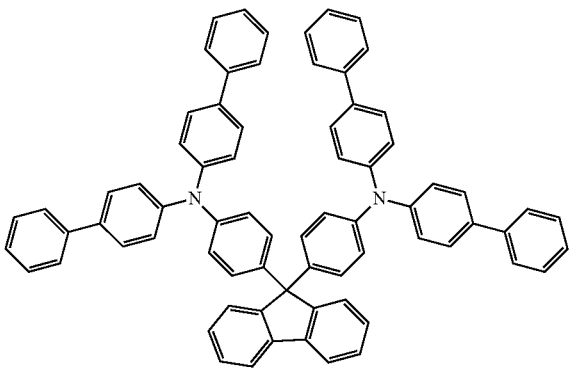

HTL1-2

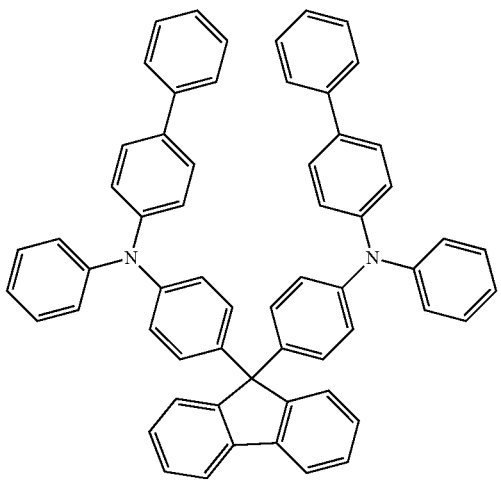

HTL1-3

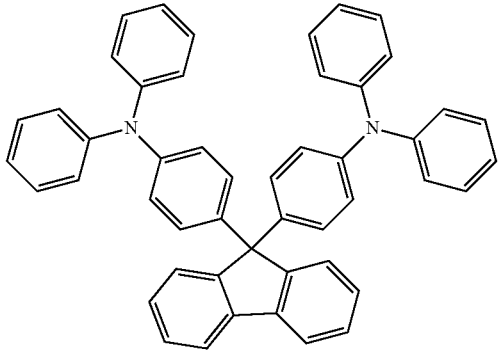

HTL1-4

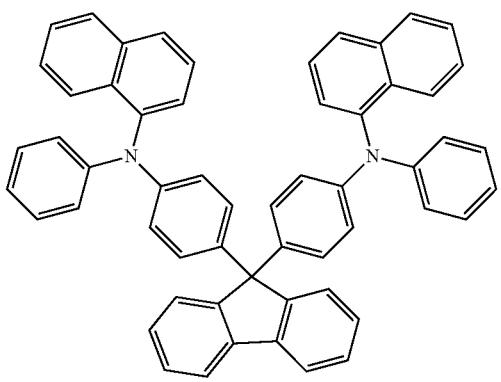

HTL1-5
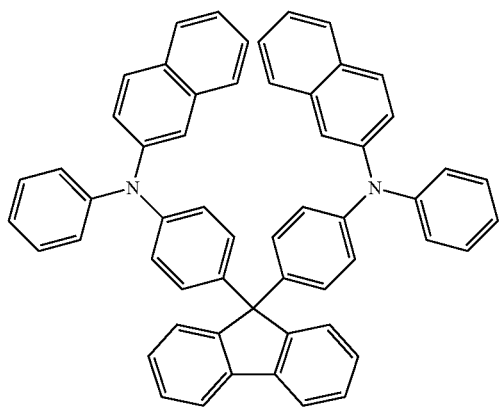
HTL1-8
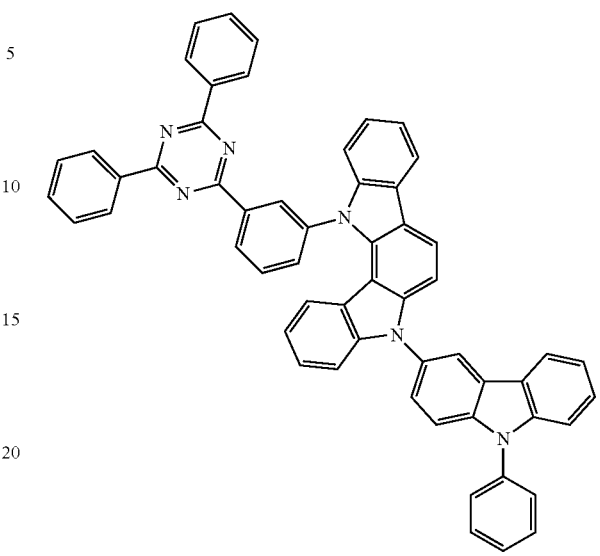
HTL1-6
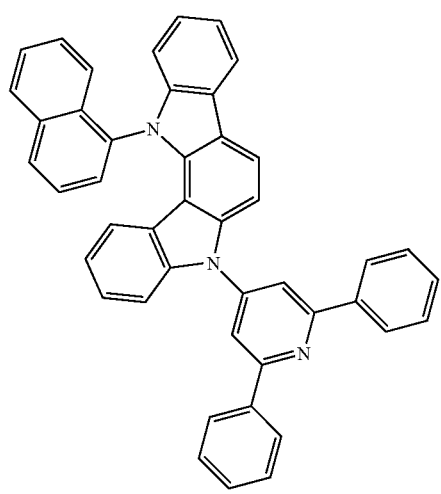
HTL1-9
HTL1-7
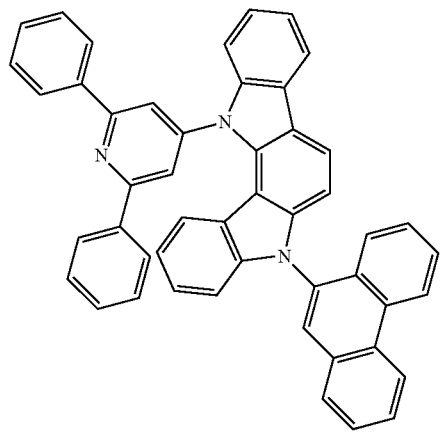
HTL1-10
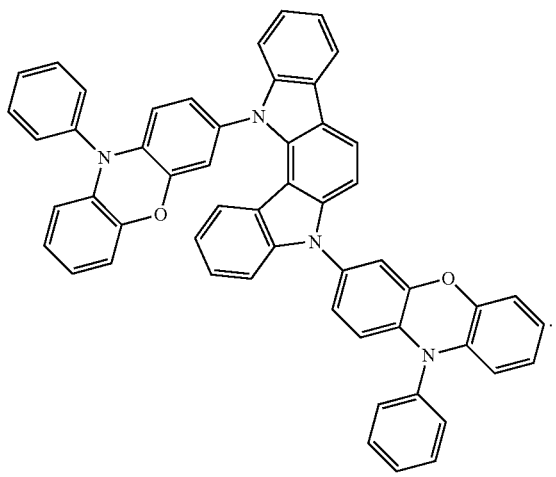

The second hole transport material has an indenofluorene structure defined by the following structural formula (3), structural formula (4), structural formula (5) or structural formula (6):

structural formula (3)

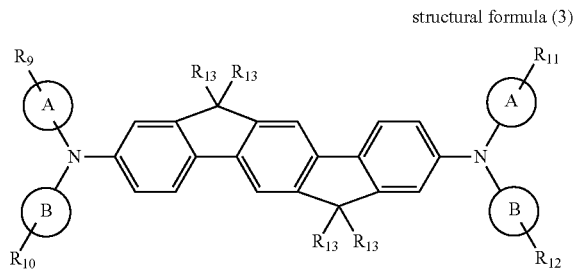

structural formula (4)

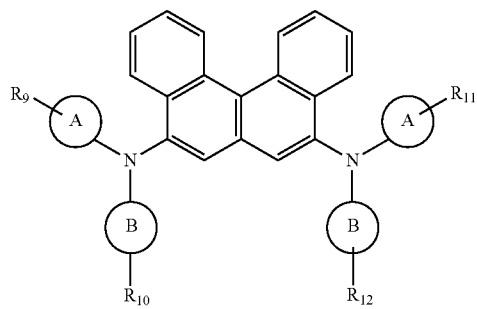

structural formula (5)

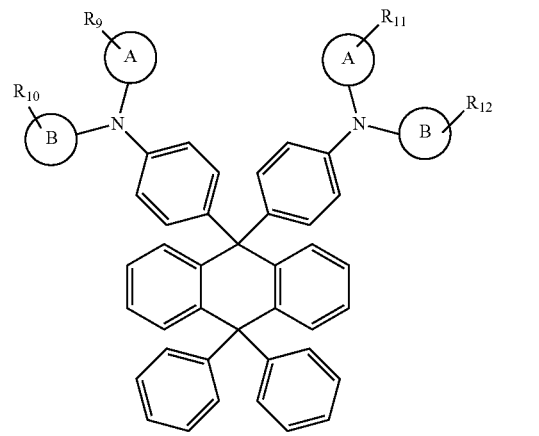

structural formula (6)

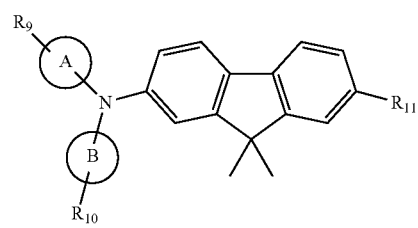

wherein, the groups of A and B are individually selected from phenyl group, naphthyl group or phenyl-amino group; the groups of $R_9$, $R_{10}$, $R_{11}$ and $R_{12}$ are identical or different, and are individually selected from $C_6$-$C_{30}$ aryl group; the group of $R_{13}$ is selected from $C_1$-$C_6$ alkyl group or hydroxyl group, preferably, the group $R_{13}$ is methyl group, ethyl group, propyl group, isopropyl group, butyl group, isobutyl group, n-amyl group or n-hexyl group.

The second hole transport material has a structure selected from the following structural formulas (HTL2-1) to (HTL2-18):

HTL2-1

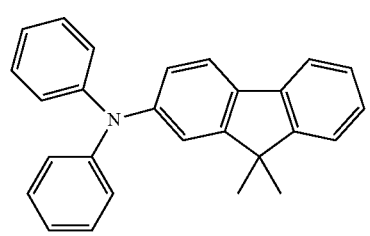

HTL2-2

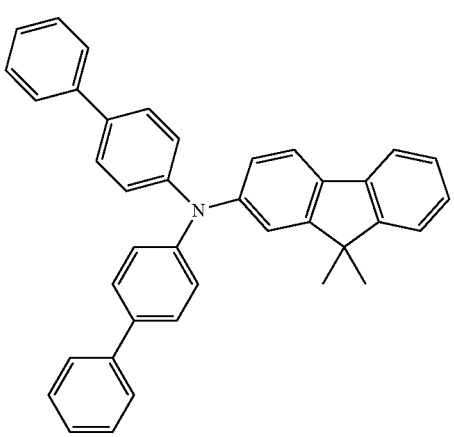

-continued
HTL2-3
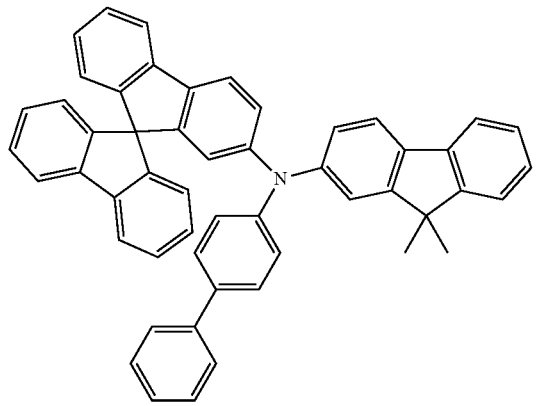
HTL2-4
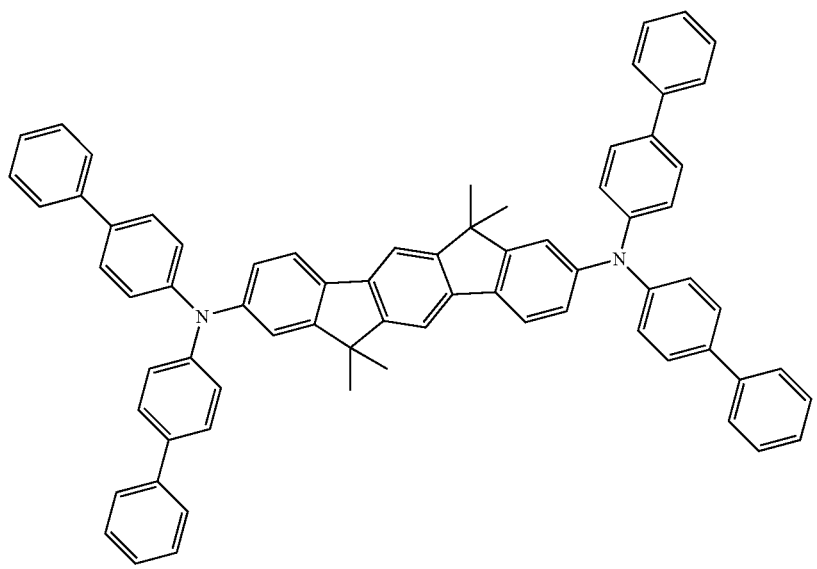
HTL2-5
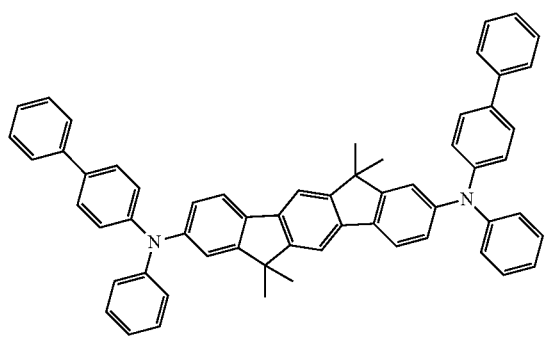
HTL2-6
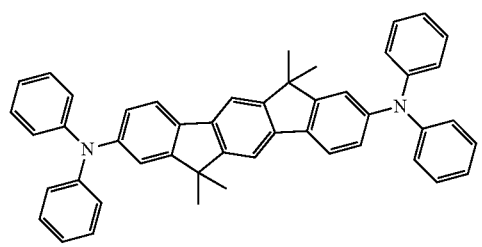

-continued
HTL2-7
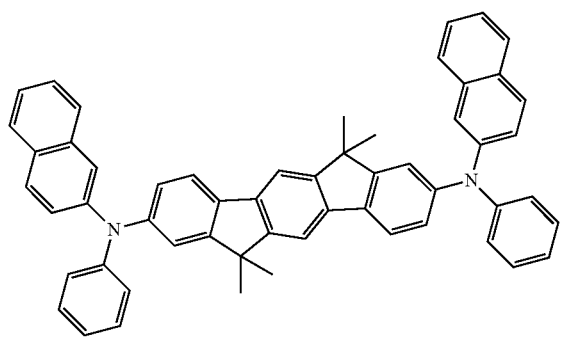
HTL2-8
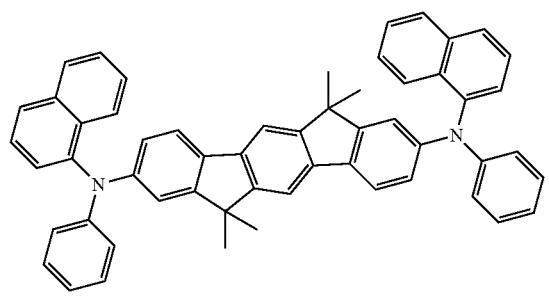
HTL2-9
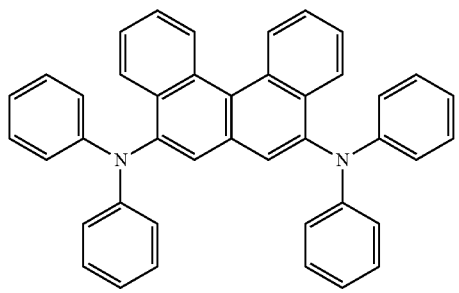
HTL2-10
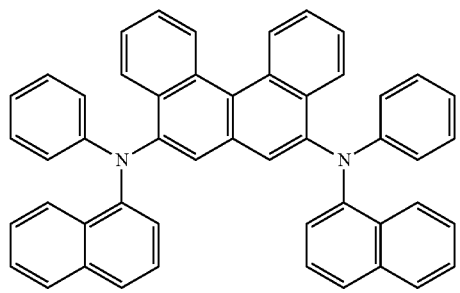
HTL2-11
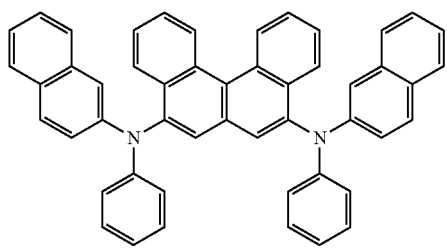
HTL2-12
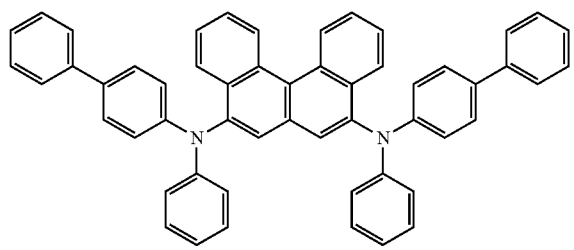
HTL2-13
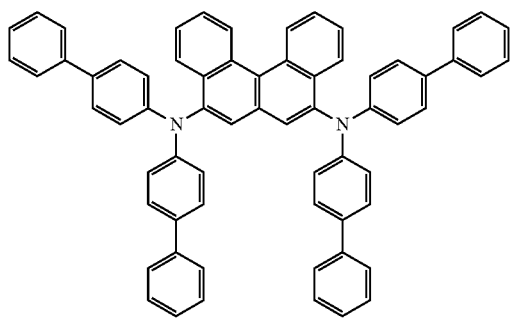
HTL2-14
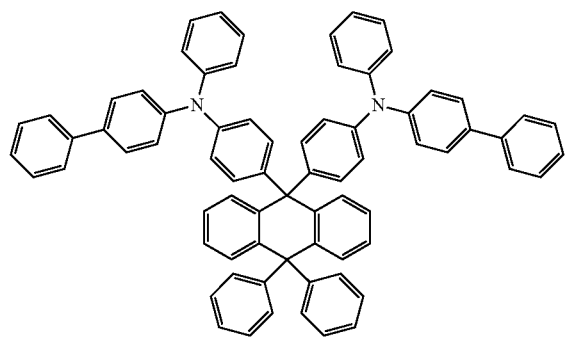

-continued

HTL2-15

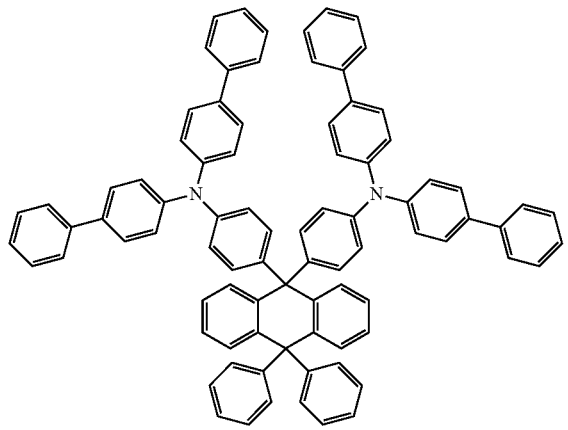

HTL2-16

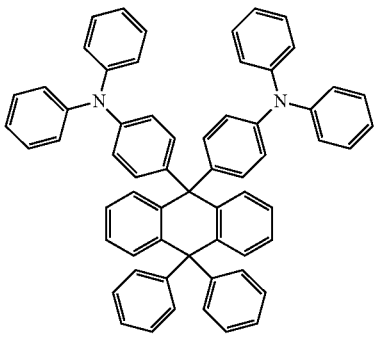

HTL2-17

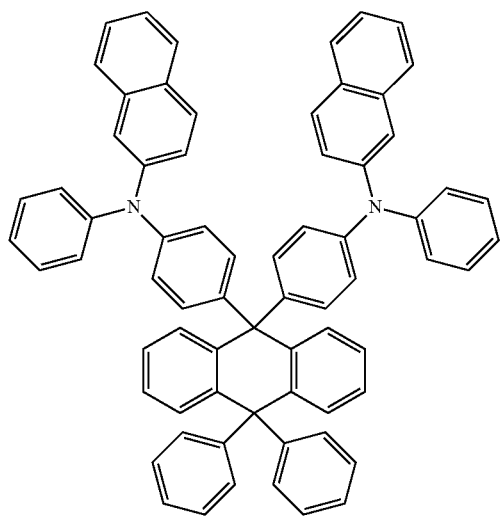

HTL2-18

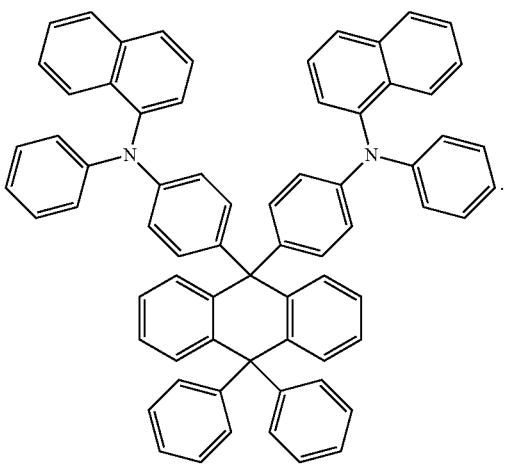

As compared to prior art, the above-mentioned technical scheme of the present invention has the following advantages:

In the organic electroluminescence display device of the present invention, optical compensation layers are arranged between the light-emitting layer and the hole transport layer, and in the evaporation coating process of the optical compensation layers with such structure, the red-light optical compensation layer and the red light emitting layer can be prepared by using the same group of mask, the green-light optical compensation layer and the green light emitting layer can be prepared by using the same group of mask, which can avoid repeated aligning operations of the masks and thus increase the process precision to a certain extent. This is because every aligning operation of the masks always has certain error, therefore, with less times of aligning operations, the error is less and the overall yield is higher.

Furthermore, the inventors of the present invention carry out creative research and daringly utilize a combination of a material having a high triplet-state energy level and a material having a high charge transfer rate to make the optical compensation layer of the present invention, and set the HOMO energy level difference between the two materials to be ≤0.2 eV, so that the optical compensation layer can be made to have different thicknesses according to requirements, and neither the light-emitting efficiency nor the drive voltage of the device is adversely affected. If the HOMO energy level difference between the two materials is too large, the first hole transport material cannot have an effect of blocking the green-light excitons.

BRIEF DESCRIPTION OF THE DRAWINGS

In order to make the content of the present invention more easy to be understood clearly, hereinafter, detailed description of the present invention is further provided according to specific embodiments of the present invention with reference to the appended drawings, wherein.

Wherein, 1—first electrode layer, 2—hole injection layer, 3—hole transport layer, 4—red light emitting layer, 5—green light emitting layer, 6—blue light emitting layer, 7—electron transport layer, 8—second electrode layer, 9—optical coupling layer, 10—red light optical compensation layer, 11—green light optical compensation layer, 12—first organic functional layer, 13—second organic functional layer.

DETAILED DESCRIPTION OF EMBODIMENTS

In order to make the objective, technical scheme and advantages of the present invention more clear, hereinafter, detailed description of implementation ways of the present invention is given below, with reference to the appended drawings.

The present invention may be implemented in many different ways, and should not be interpreted to be limited to the embodiments described herein. On the contrary, by providing these embodiments, the present disclosure is made complete and thorough, and the inventive concept of the present invention is sufficiently conveyed to those skilled in the art, wherein the present invention is defined by the claims. In the appended drawings, for the sake of clarity, dimensions and relative sizes of layers and areas might be exaggerated. It should be understood that, when one element such as a layer, an area or a substrate plate is described as "formed on" or "configured on" another element, this one element may be configured directly upon that another element, or there may exist intermediate element(s). On the contrary, when one element is described as "directly formed upon" or "directly configured upon" another element, there exist no intermediate element.

Figure 1:
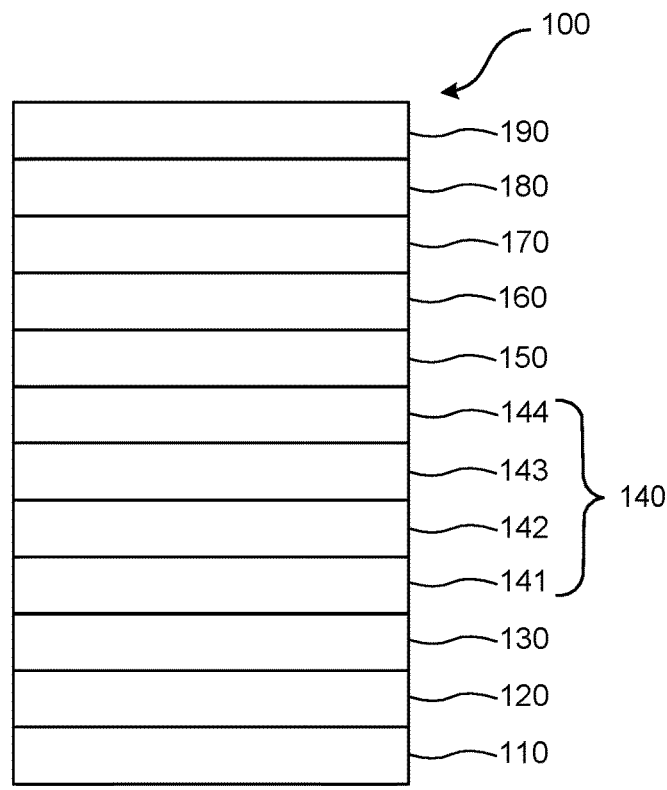
FIG. 1 is a structural schematic diagram of a light-emitting device in prior art.
Figure 2:
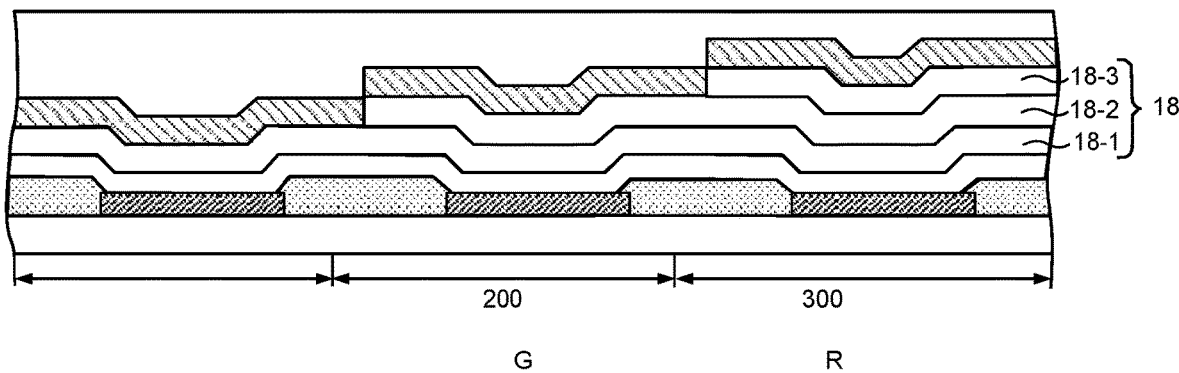
FIG. 2 is a structural schematic diagram of another light-emitting device in prior art.
Figure 3:
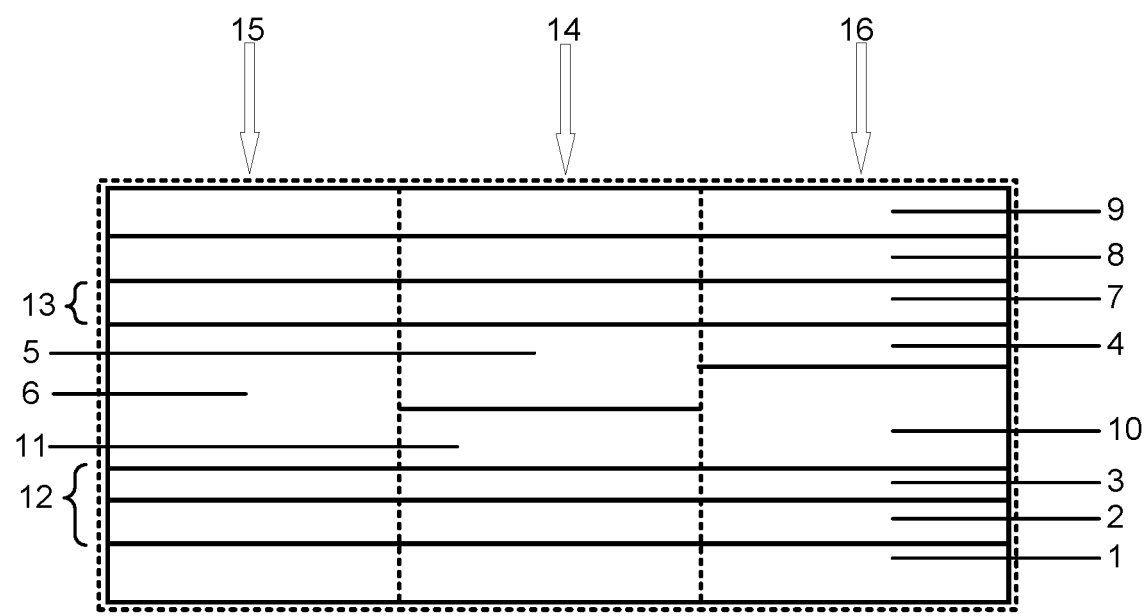
FIG. 3 is a structural schematic diagram of a light-emitting device of the present invention.

As shown in FIG. 3, it is a structural schematic diagram of an organic electroluminescence device having RGB pixel areas in accordance with the present invention.

This organic electroluminescence device having RGB pixel areas comprises a substrate (not shown in the drawing), with a first electrode layer 1 (anode layer), a plurality of organic layers, a second electrode layer 8 (cathode layer) and an optical coupling layer 9 formed in sequence on the substrate, wherein, the organic layers include a first organic functional layer 12, a light emitting layer and a second organic functional layer 13 arranged upon the first electrode layer 1, the light emitting layer comprises a red light emitting layer 4 with a thickness of $H_R$, a green light emitting layer 5 with a thickness of Ho and a blue light emitting layer 6 with a thickness of Ha, where $H_B > H_G > H_R$, and optical compensation layers are respectively arranged between the red light emitting layer 4 and the first organic functional layer 12 as well as between the green light emitting layer 5 and the first organic functional layer 12, the optical compensation layers are made of a first hole transport material and a second hole transport material, the first hole transport material has a triplet-state energy level ≥2.48 eV and a HOMO energy level ≤−5.5 eV, the second hole transport material has a HOMO energy level >−5.5 eV, and the difference between the HOMO energy level of the first hole transport material and the HOMO energy level of the second hole transport material is ≤0.2 eV.

The optical compensation layers include a red light optical compensation layer 10 arranged between the red light emitting layer 4 and the first organic functional layer 12, and a green light optical compensation layer 11 arranged between the green light emitting layer 5 and the first organic functional layer 12. In some embodiments, such as the example shown in FIG. 3, a total thickness of the red light optical compensation layer 10 plus the red light emitting layer 4, a total thickness of the green light optical compensation layer 11 plus the green light emitting layer 5, and a thickness of the blue light emitting layer 6 are substantially equal. The first hole transport material and second hole transport material contained in the red light optical compensation layer 10 has a mass ratio of 1:99 to 99:1, preferably 10:90 to 30:70. The first hole transport material and second hole transport material contained in the green light optical compensation layer 11 has a mass ratio of 5:95 to 50:50, preferably 10:90 to 30:70.

The first hole transport material has a structure defined by the following structural formula (1) or structural formula (2):

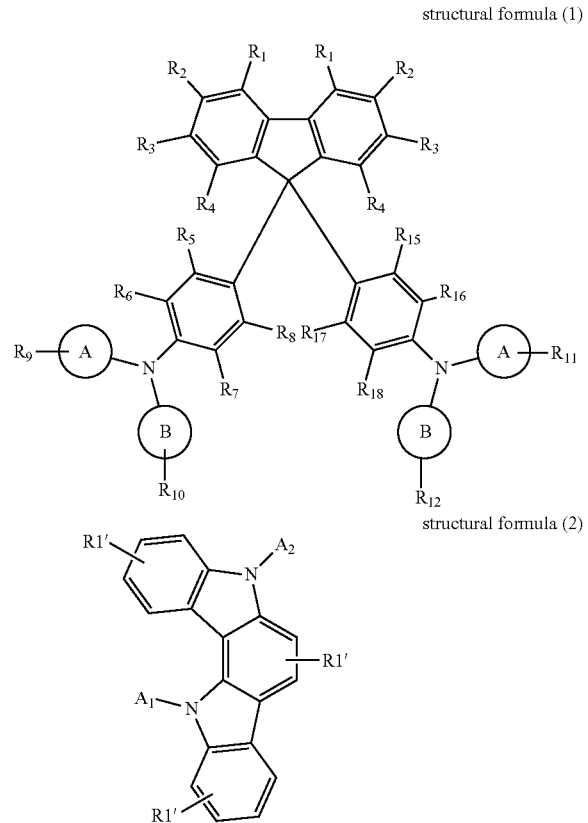

in the structural formula (1), the groups A and B are individually selected from phenyl group, naphthyl group or phenyl-amino group;

the groups of $R_1$, $R_2$, $R_3$, $R_4$, R5, $R_6$, $R_7$, $R_8$, $R_{15}$, $R_{16}$, $R_{17}$ and $R_{18}$ are identical or different, and are individually selected from hydrogen element, halogen element, CN, $NO_2$, amino group, $C_6$-$C_{30}$ fused cyclic aryl group, $C_6$-$C_{30}$ fused heterocyclic aryl group, $C_6$-$C_{20}$ alkyl group or $C_6$-$C_{30}$ alcohol group;

the groups of $R_9$, $R_{10}$, $R_{11}$ and $R_{12}$ are identical or different, and are individually selected from $C_6$-$C_{30}$ aryl group;

in the structural formula (2), the groups of A1 and A2 are individually selected from $C_6$-$C_{30}$ aryl group or $C_6$-$C_{30}$ heterocyclic aryl group, the group R1' is selected from hydrogen, alkyl group, alkoxyl group or basic group;

and the structural formula (2) also meets the following condition: at least one of the groups of A1 and A2 has a condensed ring structure.

The first hole transport material has a structure selected from the following structural formulas (HTL1-1) to (HTL1-10):

HTL1-1
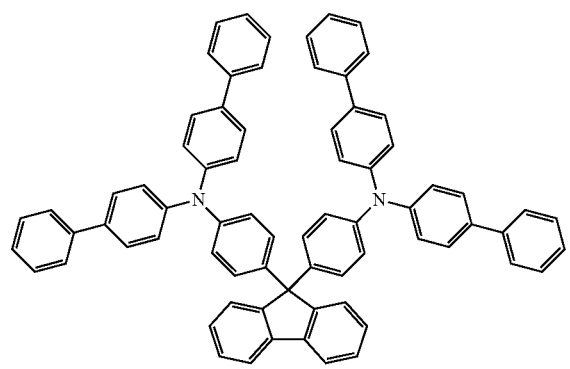
HTL1-4
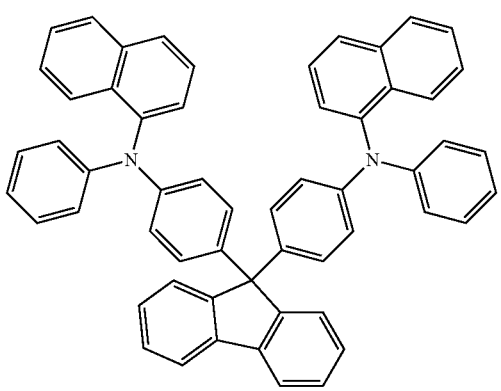
HTL1-2
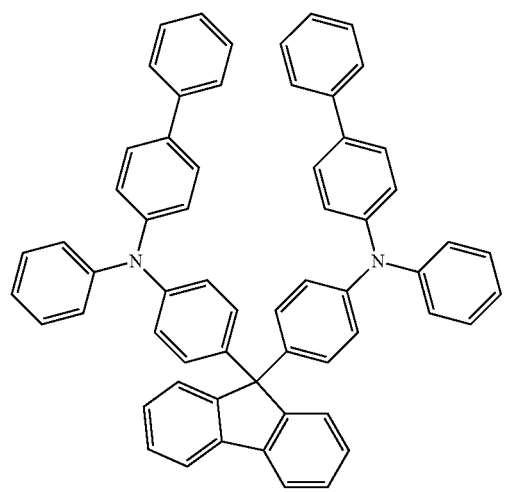
HTL1-5
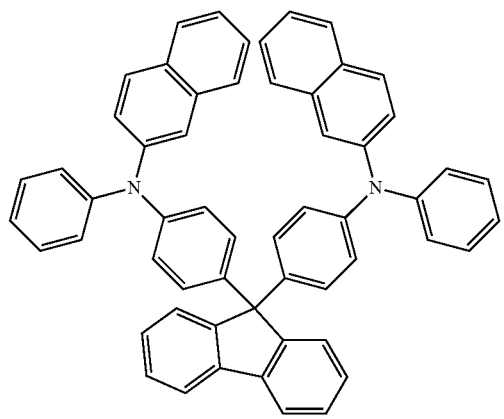
HTL1-3
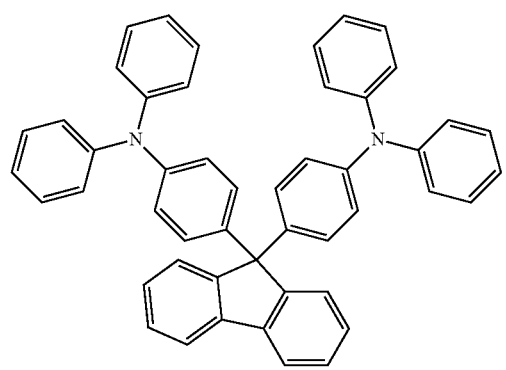
HTL1-6
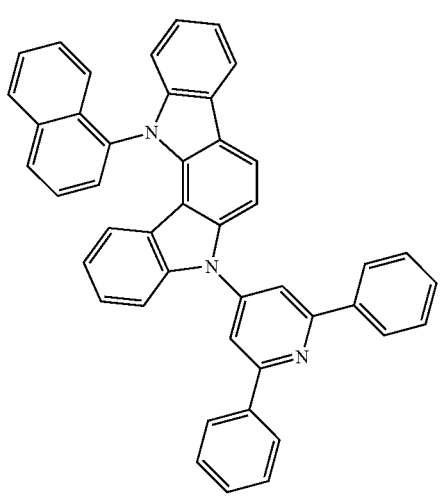

HTL1-7
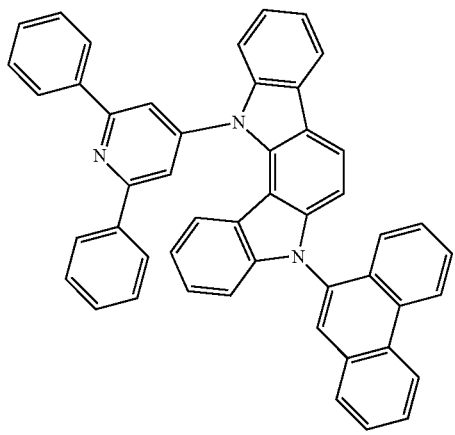
HTL1-10
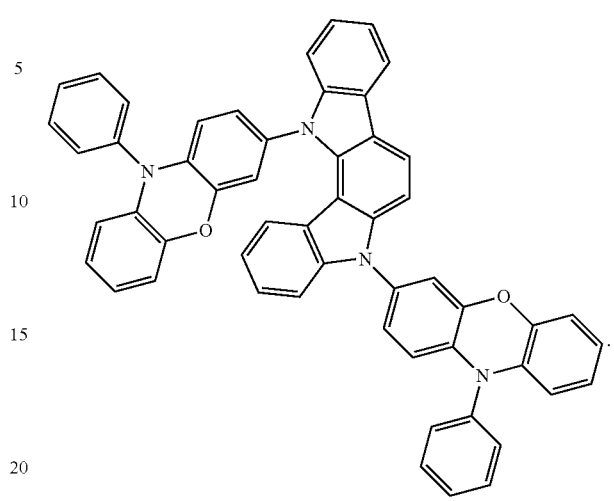
HTL1-8
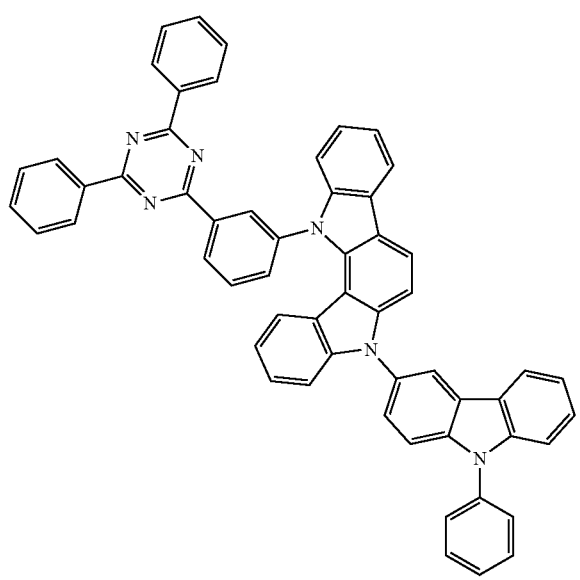
The second hole transport material has an indenofluorene structure defined by the following structural formula (3), structural formula (4), structural formula (5) or structural formula (6):
structural formula (3)
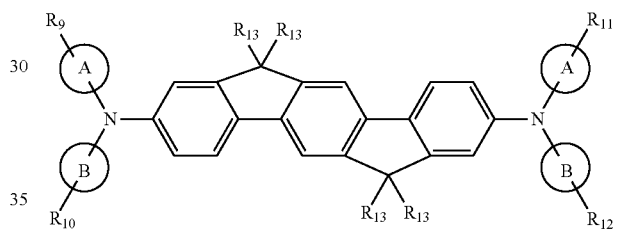
structural formula (4)
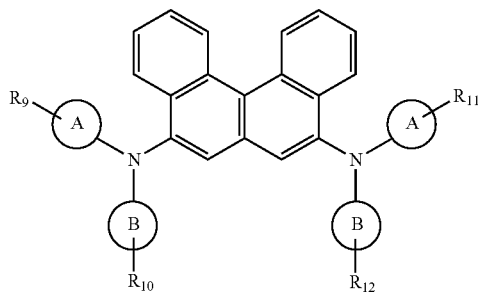
structural formula (5)
HTL1-9
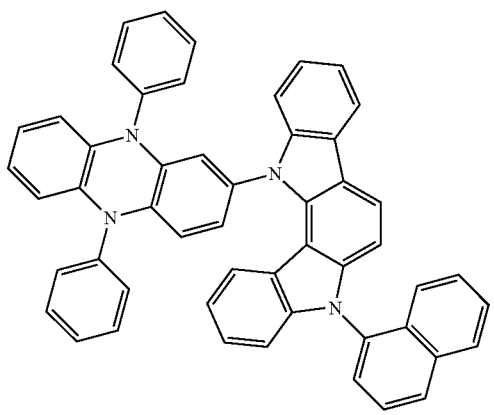
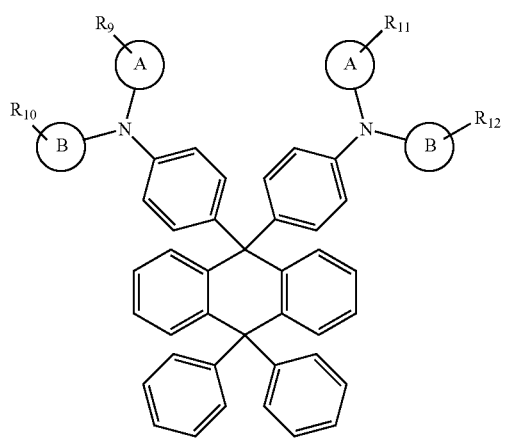

structural formula (6)

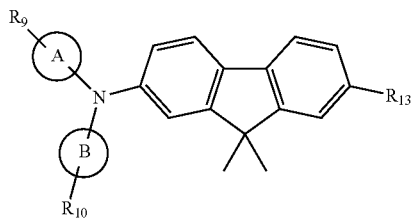

wherein, the groups of A and B are individually selected from phenyl group, napthyl group or phenyl-amino groups; the groups of $R_9$, $R_{10}$, $R_{11}$ and $R_{12}$ are identical or different, and are individually selected from $C_6$-$C_{30}$ aryl group; the group of $R_{13}$ is selected from $C_1$-$C_6$ alkyl group or hydroxyl group, preferably, the group $R_{13}$ is methyl group, ethyl group, propyl group, isopropyl group, butyl group, isobutyl group, n-amyl group or n-hexyl group.

The second hole transport material has a structure selected from the following structural formulas (HTL2-1) to (HTL2-18):

HTL2-1

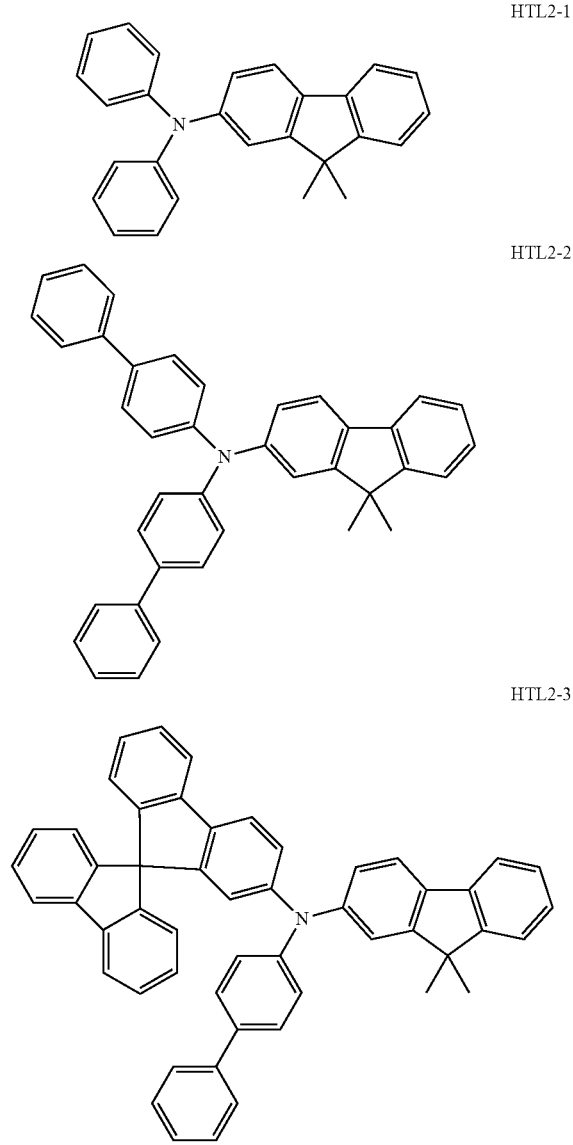

HTL2-2

HTL2-3

HTL2-4

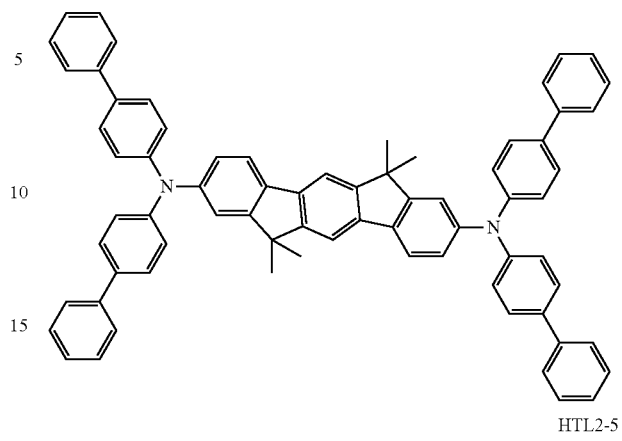

HTL2-5

HTL2-6

HTL2-7

HTL2-8

HTL2-9
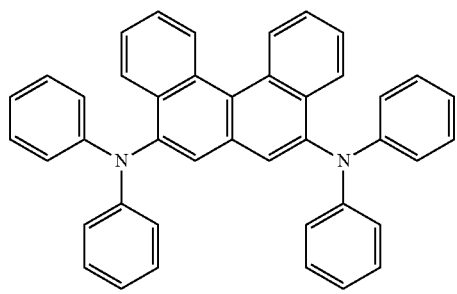
HTL2-10
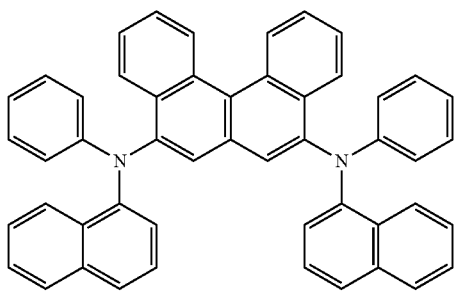
HTL2-11
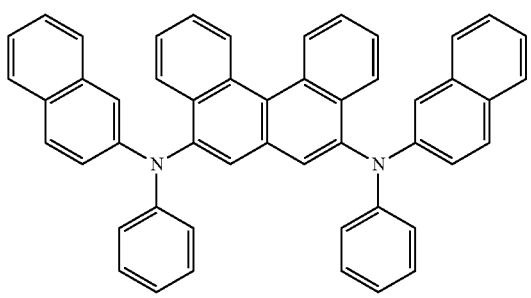
HTL2-12
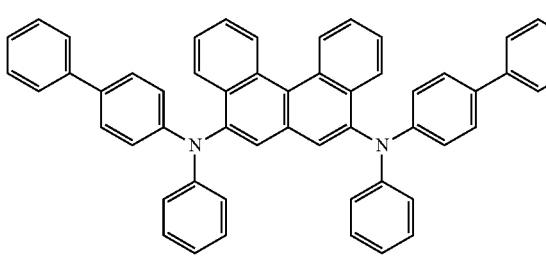
HTL2-13
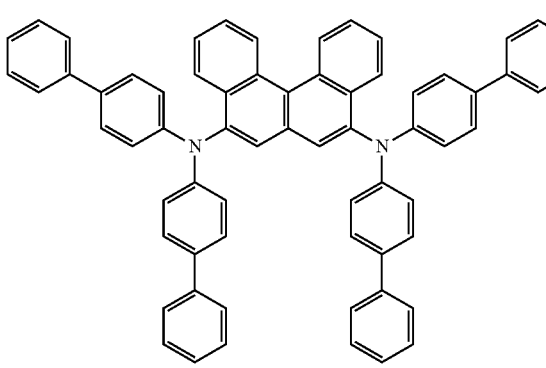
HTL2-14
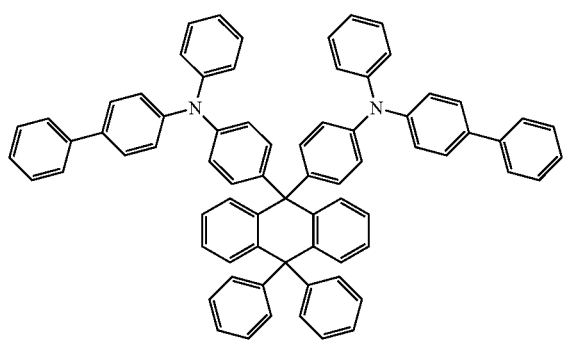
HTL2-15
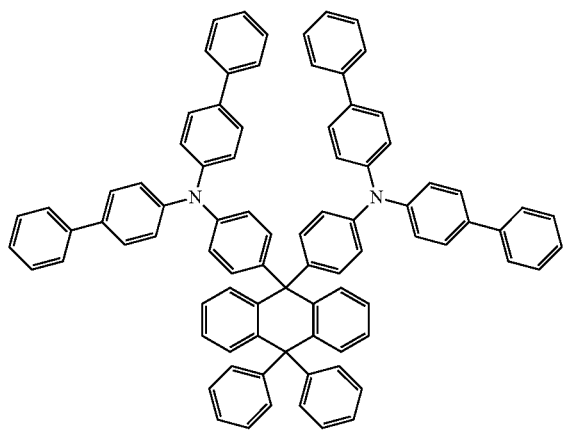
HTL2-16
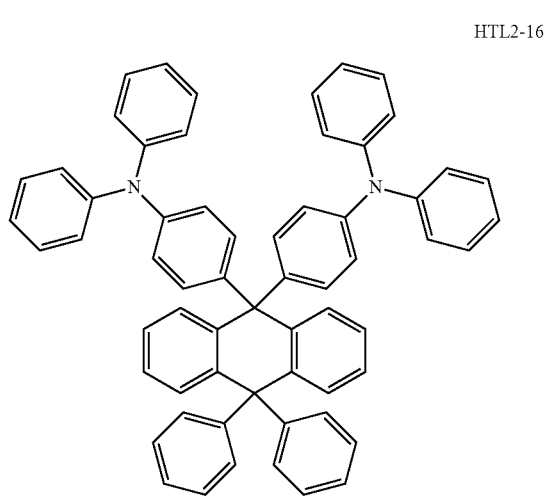

HTL2-17

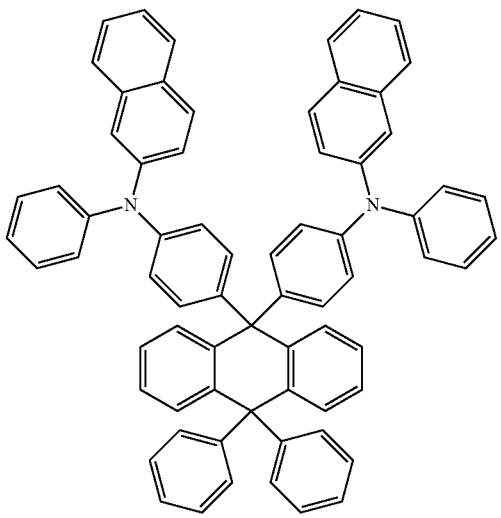

HTL2-18

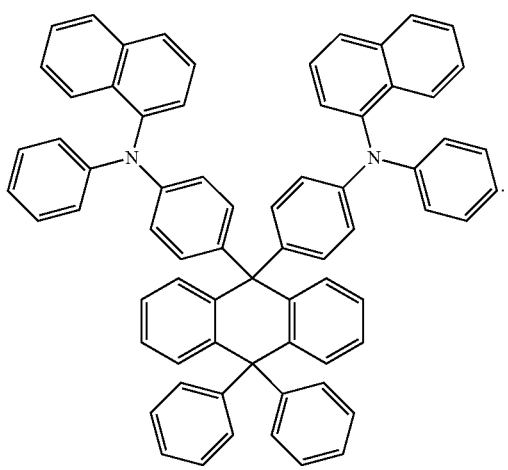

The substrate is selected from a glass substrate or a flexible substrate.

The first electrode layer 1 (anode layer) can adopt an inorganic material or an organic conducting polymer. The inorganic material is usually a metal oxide, such as indium tin oxide, zinc oxide, indium zinc oxide, or a metal with high work function, such as gold, copper, silver, preferably, it is indium tin oxide (ITO). The organic conducting polymer is preferably selected from Polythiophene/Polyethylene based sodium benzene sulfonate (hereinafter abbreviated as PEDOT:PSS) and Polyaniline (hereinafter abbreviated as PANI).

The second electrode layer 8 (cathode layer) usually adopts metal, metal compound or alloy with low work function, such as lithium, magnesium, calcium, strontium, aluminum, indium. In the present invention, the electron transport layer 7 is preferably doped with an active metal such as Li, K, Cs which is preferably prepared by evaporation coating of an alkali metal compound.

The hole injection layer 2 (HIL) has a matrix material that is preferably HAT, 4,4-(N-3-methyl-phenyl-N-phenyl-amino)-triphenylamine (m-MTDATA), 4,4TDAT, or tri-(N-2-naphthyl-N-phenyl-amino)-triphenylamine (2-TNATA).

The hole transport layer 3 (HTL) has a matrix material that may adopt a low molecular material of the arylamine type or the branched polymer species, preferably N,N-di-(1-naphthyl)-N,N-diphenyl-1,1'-biphenyl-4,4'-diamine (NPB).

The electron transport layer 7 has a material selected from $Alq_3$, Bphen, BAlq or selected from the following materials:

ETL-1

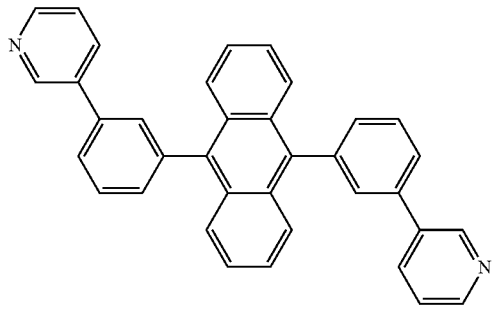

ETL-2

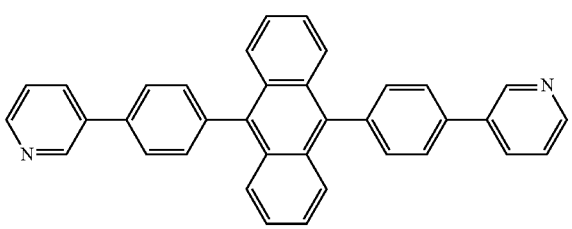

ETL-3

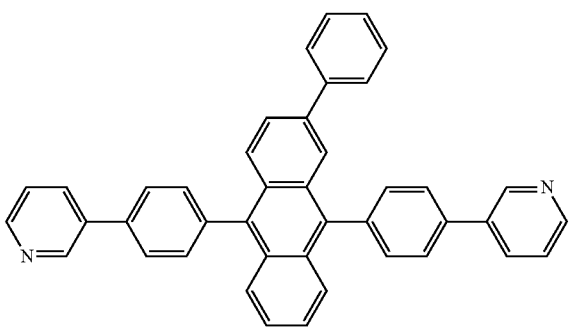

ETL-4

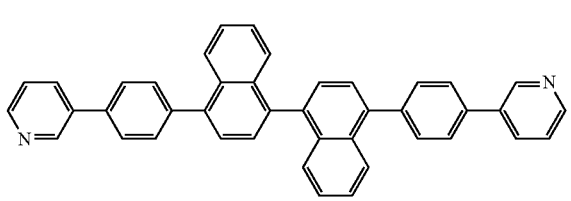

The blue light emitting layer 6 usually adopts a host material selected from ADN and its derivatives, together with a dye having a molecular structure selected from the following formula (BD-1) or formula (BD-2):

(BD-1)

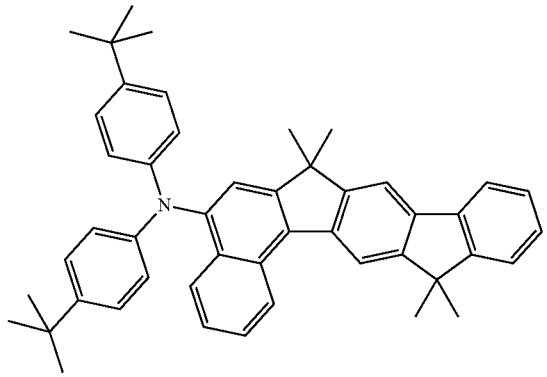

(BD-2)

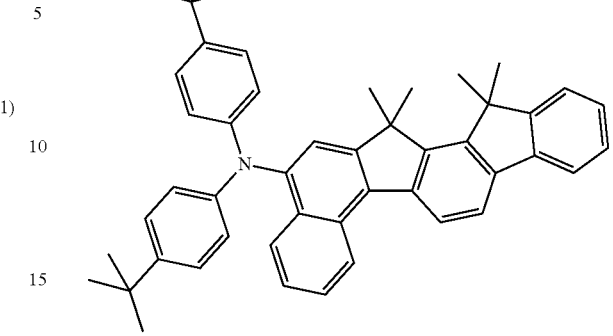

The red light emitting layer 4 usually adopts the following material: $Ir(piq)_3$, $Ir(piq)_2(acac)$, $Btp_2Ir(acac)$, $Ir(MDQ)_2(acac)$, $Ir(DBQ)_2(acac)$, $Ir(fbi)_2(acac)$, $Ir(2\text{-}phq)_3$, $Ir(2\text{-}phq)_2(acac)$, $Ir(bt)_2(acac)$, PtOEP, etc.

The green light emitting layer 5 usually adopts the following material: $Ir(ppy)_3$, $Ir(ppy)_2(acac)$, etc.

The structural formulas of the main chemical substances in the present invention are explained as follows:

| Abbreviation | Structural Formula |
|---|---|
| NPB | |
| HAT | |
| MTDATA | |

| Abbreviation | Structural Formula |
|---|---|
| Ir(ppy)$_3$ | |
| Ir(MDQ)$_2$(acac) | |
| ADN | |
| BPhen | |

Some embodiments are given below, for specifically explaining the technical scheme of the present invention with reference to the appended drawings. It should be noted that, the following embodiments are only intended to help understanding the present invention, not to limit the present invention.

The organic electroluminescence device of Embodiments 1-14 has the following structures, and the differences thereof are different materials used by the red light optical compensation layer 10 and the green light optical compensation layer 11.

Blue light emitting area 15 (within the leftmost dotted line block in FIG. 3): ITO/HAT(10 nm)/MTDATA(100 nm)/NPB(20 nm)/ADN(30 nm):BD-1/ETL-1(35 nm)/Mg:Ag (20 nm)/MTDATA(50 nm)

Green light emitting area 14 (within the middle dotted line block in FIG. 3): ITO/HAT(10 nm)/MTDATA(100 nm)/NPB(20 nm)/HTL1:HTL2(60 nm)/CBP(30 nm):Ir(ppy)3/ET L-1(35 nm)/Mg:Ag(20 nm)/MTDATA(50 nm)

Red light emitting area 16 (within the rightmost dotted line block in FIG. 3): ITO/HAT(10 nm)/MTDATA(100 nm)/NPB(20 nm)/HTL1:HTL2(10 nm)/CBP(30 nm):Ir(mdq)2(acac)/ETL-1(35 nm)/Mg:Ag(20 nm)/MTDATA (50 nm).

Embodiment 1

Wherein, the first hole transport material HTL1 has a structure as shown by formula HTL-1, and the second hole transport material HTL2 has a structure as shown by formula HTL2-1;

In the red light optical compensation layer 10, the first hole transport material HTL1-1 and second hole transport material HTL2-1 have a mass ratio of 50:50;

In the green light optical compensation layer 11, the first hole transport material HTL1-1 and second hole transport material HTL2-1 have a mass ratio of 50:50.

Embodiment 2

Wherein, the first hole transport material HTL1 has a structure as shown by formula HTL1-2, and the second hole transport material HTL2 has a structure as shown by formula HTL2-2;

In the red light optical compensation layer 10, the first hole transport material HTL1-2 and second hole transport material HTL2-2 have a mass ratio of 1:99;

In the green light optical compensation layer 11, the first hole transport material HTL1-2 and second hole transport material HTL2-2 have a mass ratio of 50:50.

Embodiment 3

Wherein, the first hole transport material HTL1 has a structure as shown by formula HTL1-3, and the second hole transport material HTL2 has a structure as shown by formula HTL2-3;

In the red light optical compensation layer 10, the first hole transport material HTL1-3 and second hole transport material HTL2-3 have a mass ratio of 99:1;

In the green light optical compensation layer 11, the first hole transport material HTL1-3 and second hole transport material HTL2-3 have a mass ratio of 95:5.

Embodiment 4

Wherein, the first hole transport material HTL1 has a structure as shown by formula HTL1-4, and the second hole transport material HTL2 has a structure as shown by formula HTL2-18;

In the red light optical compensation layer 10, the first hole transport material HTL1-4 and second hole transport material HTL2-18 have a mass ratio of 90:10;

In the green light optical compensation layer 11, the first hole transport material HTL-4 and second hole transport material HTL2-18 have a mass ratio of 5:95.

Embodiment 5

Wherein, the first hole transport material HTL1 has a structure as shown by formula HTL1-5, and the second hole transport material HTL2 has a structure as shown by formula HTL2-16;

In the red light optical compensation layer 10, the first hole transport material HTL1-5 and second hole transport material HTL2-16 have a mass ratio of 70:30;

In the green light optical compensation layer 11, the first hole transport material HTL1-5 and second hole transport material HTL2-16 have a mass ratio of 15:85.

Embodiment 6

Wherein, the first hole transport material HTL1 has a structure as shown by formula HTL1-6, and the second hole transport material HTL2 has a structure as shown by formula HTL2-15;

In the red light optical compensation layer 10, the first hole transport material HTL1-6 and second hole transport material HTL2-15 have a mass ratio of 40:60;

In the green light optical compensation layer 11, the first hole transport material HTL1-6 and second hole transport material HTL2-15 have a mass ratio of 40:60.

Embodiment 7

Wherein, the first hole transport material HTL1 has a structure as shown by formula HTL1-7, and the second hole transport material HTL2 has a structure as shown by formula HTL2-14;

In the red light optical compensation layer 10, the first hole transport material HTL1-7 and second hole transport material HTL2-14 have a mass ratio of 50:50;

In the green light optical compensation layer 11, the first hole transport material HTL1-7 and second hole transport material HTL2-14 have a mass ratio of 30:70.

Embodiment 8

Wherein, the first hole transport material HTL1 has a structure as shown by formula HTL1-8, and the second hole transport material HTL2 has a structure as shown by formula HTL2-13;

In the red light optical compensation layer 10, the first hole transport material HTL1-8 and second hole transport material HTL2-13 have a mass ratio of 35:65;

In the green light optical compensation layer 11, the first hole transport material HTL1-8 and second hole transport material HTL2-13 have a mass ratio of 25:75.

Embodiment 9

Wherein, the first hole transport material HTL1 has a structure as shown by formula HTL1-9, and the second hole transport material HTL2 has a structure as shown by formula HTL2-12;

In the red light optical compensation layer 10, the first hole transport material HTL1-9 and second hole transport material HTL2-12 have a mass ratio of 90:10;

In the green light optical compensation layer 11, the first hole transport material HTL-9 and second hole transport material HTL2-12 have a mass ratio of 45:55.

Embodiment 10

Wherein, the first hole transport material HTL1 has a structure as shown by formula HTL1-10, and the second hole transport material HTL2 has a structure as shown by formula HTL2-11 or HTL2-6;

In the red light optical compensation layer 10, the first hole transport material HTL1-10 and second hole transport material HTL2-11 have a mass ratio of 45:55;

In the green light optical compensation layer 11, the first hole transport material HTL1-10 and second hole transport material HTL2-6 have a mass ratio of 10:90.

Embodiment 11

Wherein, the first hole transport material HTL1 has a structure as shown by formula HTL1-1, and the second hole transport material HTL2 has a structure as shown by formula HTL2-10;

In the red light optical compensation layer 10, the first hole transport material HTL1-1 and second hole transport material HTL2-10 have a mass ratio of 95:5;

In the green light optical compensation layer 11, the first hole transport material HTL1-1 and second hole transport material HTL2-10 have a mass ratio of 5:95.

Embodiment 12

Wherein, the first hole transport material HTL1 has a structure as shown by formula HTL1-3, and the second hole transport material HTL2 has a structure as shown by formula HTL2-9 or HTL2-17;

In the red light optical compensation layer 10, the first hole transport material HTL1-3 and second hole transport material HTL2-17 have a mass ratio of 55:45;

In the green light optical compensation layer 11, the first hole transport material HTL-3 and second hole transport material HTL2-9 have a mass ratio of 20:80.

Embodiment 13

Wherein, the first hole transport material HTL1 has a structure as shown by formula HTL1-5, and the second hole transport material HTL2 has a structure as shown by formula HTL2-8 or HTL2-4;

In the red light optical compensation layer 10, the first hole transport material HTL1-5 and second hole transport material HTL2-8 have a mass ratio of 55:45;

In the green light optical compensation layer 11, the first hole transport material HTL1-5 and second hole transport material HTL2-4 have a mass ratio of 20:80.

Embodiment 14

Wherein, the first hole transport material HTL1 has a structure as shown by formula HTL1-8, and the second hole transport material HTL2 has a structure as shown by formula HTL2-5 or HTL2-7;

In the red light optical compensation layer 10, the first hole transport material HTL1-8 and second hole transport material HTL2-7 have a mass ratio of 30:70;

In the green light optical compensation layer 11, the first hole transport material HTL1-8 and second hole transport material HTL2-5 have a mass ratio of 40:60.

Comparison Example

Blue light emitting area 15 (within the leftmost dotted line block in FIG. 3): ITO/HAT(10 nm)/MTDATA(100 nm)/NPB(20 nm)/ADN(30 nm):BD-1/ETL-1(35 nm)/Mg:Ag (20 nm)/MTDATA(50 nm)

Green light emitting area 14 (within the middle dotted line block in FIG. 3): ITO/HAT(10 nm)/MTDATA(160 nm)/NPB(20 nm)/CBP(30 nm):Ir(ppy)$_3$/ETL-1(35 nm)/Mg:Ag (20 nm)/MTDATA(50 nm)

Red light emitting area 16 (within the rightmost dotted line block in FIG. 3): ITO/HAT(10 nm)/MTDATA(210 nm)/NPB(20 nm)/CBP(30 nm):Ir(mdq)$_2$(acac)/ETL-1 (35 nm)/Mg:Ag(20 nm)/MTDATA(50 nm)

The test results of the devices are listed below:

|  | Blue light efficiency (cd/A) | Green light efficiency (cd/A) | Red light efficiency (cd/A) |
| --- | --- | --- | --- |
| Embodiment 1 | 4.3 | 70.2 | 29.3 |
| Embodiment 2 | 4.3 | 66.3 | 29.8 |
| Embodiment 3 | 4.3 | 69.5 | 32.1 |
| Embodiment 4 | 4.3 | 72.5 | 30.6 |
| Embodiment 5 | 4.3 | 72.1 | 28.4 |
| Embodiment 6 | 4.3 | 67.0 | 34.2 |
| Embodiment 7 | 4.3 | 69.4 | 30.3 |
| Embodiment 8 | 4.3 | 75.1 | 36.7 |
| Embodiment 9 | 4.3 | 65.2 | 33.1 |
| Embodiment 10 | 4.3 | 64.2 | 27.0 |
| Embodiment 11 | 4.3 | 69.0 | 28.9 |
| Embodiment 12 | 4.3 | 65.9 | 27.0 |
| Embodiment 13 | 4.3 | 71.5 | 33.5 |
| Embodiment 14 | 4.3 | 72.2 | 30.4 |
| Comparison Example | 4.3 | 63.3 | 26.9 |

As indicated by the test results, because the optical compensation layers is made of a combination of a hole transport material having a high energy level and a material having a high charge transfer rate, the light emitting efficiencies of the red light emitting layer and the green light emitting layer are significantly increased.

Apparently, the aforementioned embodiments are merely examples illustrated for clearly describing the present invention, rather than limiting the implementation ways thereof. For those skilled in the art, various changes and modifications in other different forms can be made on the basis of the aforementioned description. It is unnecessary and impossible to exhaustively list all the implementation ways herein. However, any obvious changes or modifications derived from the aforementioned description are intended to be embraced within the protection scope of the present invention.

The invention claimed is:

1. An organic electroluminescence device having RGB pixel areas, comprising a substrate, with a first electrode layer, a plurality of organic layers and a second electrode layer formed in sequence on the substrate, wherein, the organic layers include a first organic functional layer, a light emitting layer and a second organic functional layer arranged upon the first electrode layer, the light emitting layer comprises a red light emitting layer, a green light emitting layer and a blue light emitting layer, wherein, the organic electroluminescence device further comprises optical compensation layers including a red light optical compensation layer arranged between the red light emitting layer and the first organic functional layer as well as a green light optical compensation layer arranged between the green light emitting layer and the first organic functional layer, the optical compensation layers are made of a first hole transport material and a second hole transport material, the first hole transport material has a triplet-state energy level ≥2.48 eV and a HOMO energy level ≤−5.5 eV, the second hole transport material has a HOMO energy level >−5.5 eV, and the difference between the HOMO energy level of the first hole transport material and the HOMO energy level of the second hole transport material is ≤0.2 eV;

wherein a total thickness of the red light optical compensation layer plus the red light emitting layer, a total thickness of the green light optical compensation layer plus the green light emitting layer, and a thickness of the blue light emitting layer are substantially equal;

wherein top surfaces of the red light emitting layer, the green light emitting layer and the blue light emitting layer are substantially coplanar.

2. The organic electroluminescence device having RGB pixel areas of claim 1, wherein, the first hole transport material and second hole transport material contained in the red light optical compensation layer has a mass ratio of 1:99 to 99:1.

3. The organic electroluminescence device having RGB pixel areas of claim 1, wherein, the first hole transport material and second hole transport material contained in the green light optical compensation layer has a mass ratio of 5:95 to 50:50.

4. The organic electroluminescence device having RGB pixel areas of claim 3, wherein, the first hole transport material and second hole transport material contained in the green light optical compensation layer has a mass ratio of 10:90 to 30:70.

5. An organic electroluminescence device having RGB pixel areas, comprising a substrate, with a first electrode layer, a plurality of organic layers and a second electrode layer formed in sequence on the substrate, wherein, the organic layers include a first organic functional layer, a light emitting layer and a second organic functional layer arranged upon the first electrode layer, the light emitting layer comprises a red light emitting layer, a green light emitting layer and a blue light emitting layer, wherein,
the organic electroluminescence device further comprises optical compensation layers including a red light optical compensation layer arranged between the red light emitting layer and the first organic functional layer as well as a green light optical compensation layer arranged between the green light emitting layer and the first organic functional layer, the optical compensation layers are made of a first hole transport material and a second hole transport material, the first hole transport material has a triplet-state energy level ≥2.48 eV and a HOMO energy level ≤−5.5 eV, the second hole transport material has a HOMO energy level >−5.5 eV, and the difference between the HOMO energy level of the first hole transport material and the HOMO energy level of the second hole transport material is ≤0.2 eV;
wherein a total thickness of the red light optical compensation layer plus the red light emitting layer, a total thickness of the green light optical compensation layer plus the green light emitting layer, and a thickness of the blue light emitting layer are substantially equal;
wherein top surfaces of the red light emitting layer, the green light emitting layer and the blue light emitting layer are substantially coplanar;
wherein, the first hole transport material has a structure defined by the following structural formula (2):

structural formula (2)

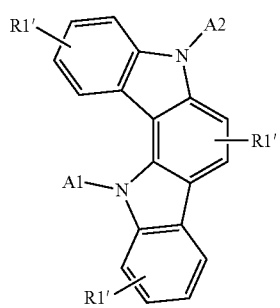

in the structural formula (2), the groups of A1 and A2 are individually selected from $C_6$-$C_{30}$ aryl group or $C_6$-$C_{30}$ heterocyclic aryl group, the group R1' is selected from hydrogen, alkyl group, alkoxyl group or basic group;
and the structural formula (2) also meets the following condition: at least one of the groups of A1 and A2 has a condensed ring structure.

6. The organic electroluminescence device having RGB pixel areas of claim 5, wherein, the first hole transport material has a structure selected from the following structural formulas (HTL1-6), (HTL1-7), and (HTL1-9):

HTL1-6

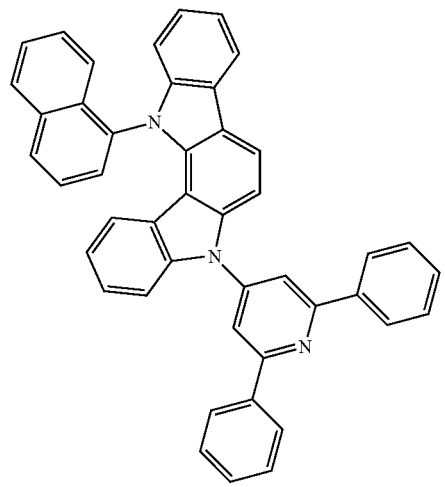

HTL1-7

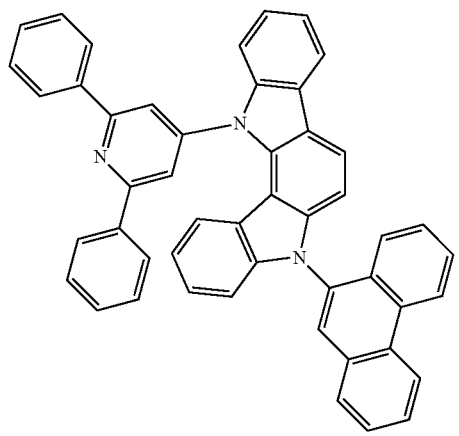

HTL1-9

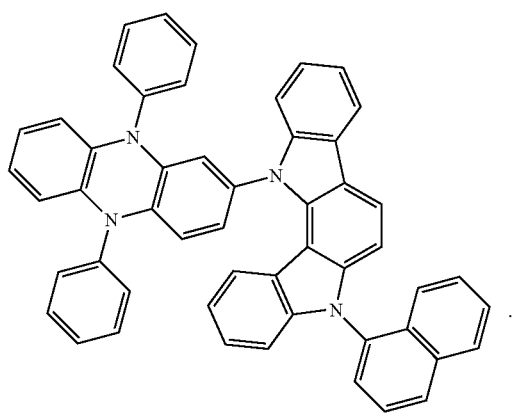

7. An organic electroluminescence device having RGB pixel areas, comprising a substrate, with a first electrode layer, a plurality of organic layers and a second electrode layer formed in sequence on the substrate, wherein, the organic layers include a first organic functional layer, a light emitting layer and a second organic functional layer arranged upon the first electrode layer, the light emitting layer comprises a red light emitting layer, a green light emitting layer and a blue light emitting layer, wherein,
the organic electroluminescence device further comprises optical compensation layers including a red light optical compensation layer arranged between the red light emitting layer and the first organic functional layer as well as a green light optical compensation layer arranged between the green light emitting layer and the first organic functional layer, the optical compensation layers are made of a first hole transport material and a second hole transport material, the first hole transport material has a triplet-state energy level ≥2.48 eV and a HOMO energy level ≤−5.5 eV, the second hole transport material has a HOMO energy level >−5.5 eV, and the difference between the HOMO energy level of the first hole transport material and the HOMO energy level of the second hole transport material is ≤0.2 eV;
wherein a total thickness of the red light optical compensation layer plus the red light emitting layer, a total thickness of the green light optical compensation layer plus the green light emitting layer, and a thickness of the blue light emitting layer are substantially equal;
wherein top surfaces of the red light emitting layer, the green light emitting layer and the blue light emitting layer are substantially coplanar;
wherein, the second hole transport material has a structure defined by the following structural formula (5):

structural formula (5)

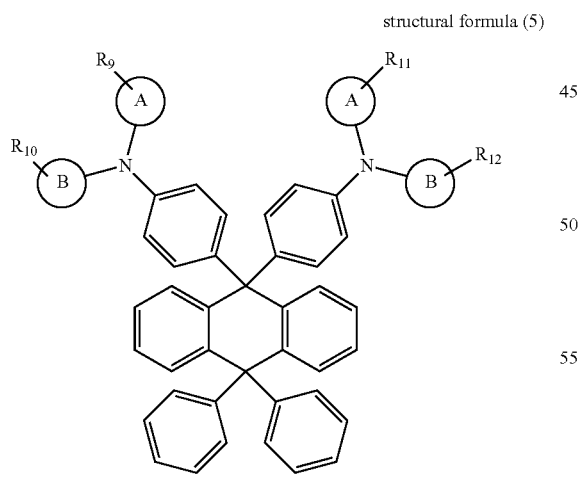

wherein, the groups of A and B are individually selected from phenyl group, naphthyl group or phenyl-amino group;
the groups of $R_9$, $R_{10}$, $R_{11}$ and $R_{12}$ are identical or different, and are individually selected from $C_6$-$C_{30}$ aryl group.

8. The organic electroluminescence device having RGB pixel areas of claim 7, wherein, the second hole transport material has a structure selected from the following structural formulas (HTL2-14) to (HTL2-18):

HTL2-14

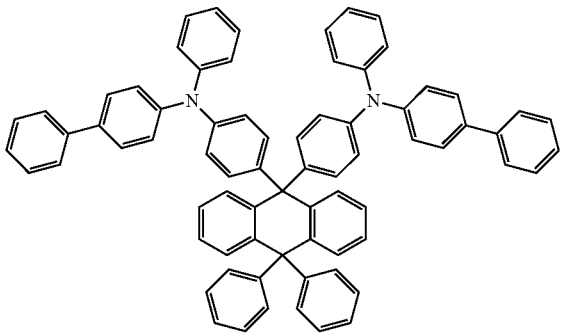

HTL2-15

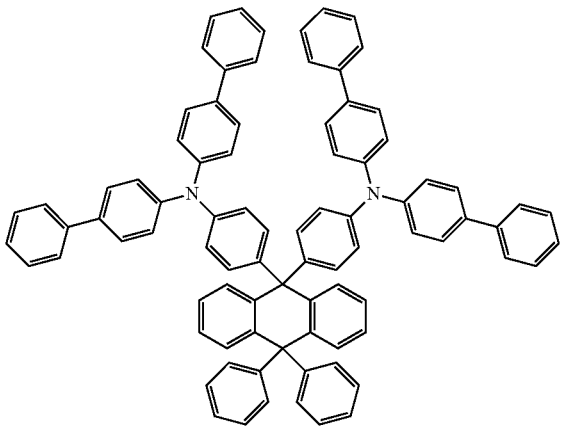

HTL2-16

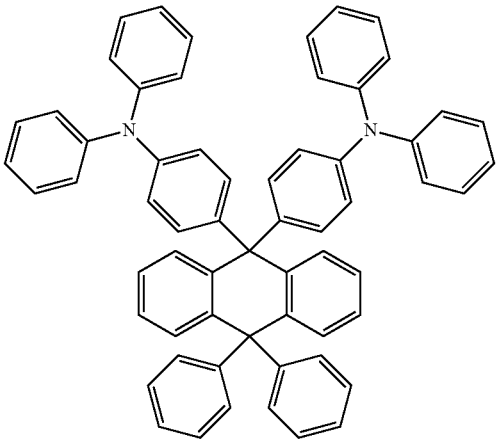

HTL2-17
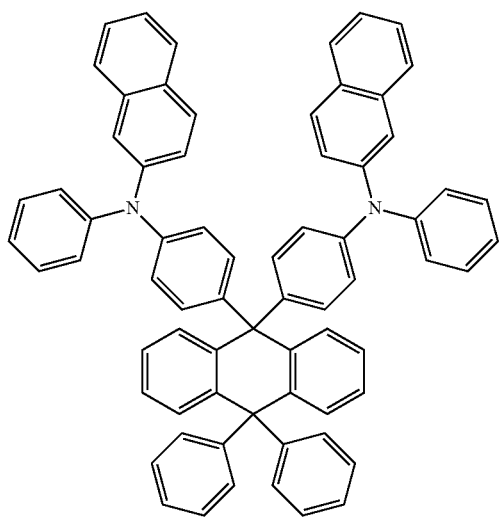
HTL2-18
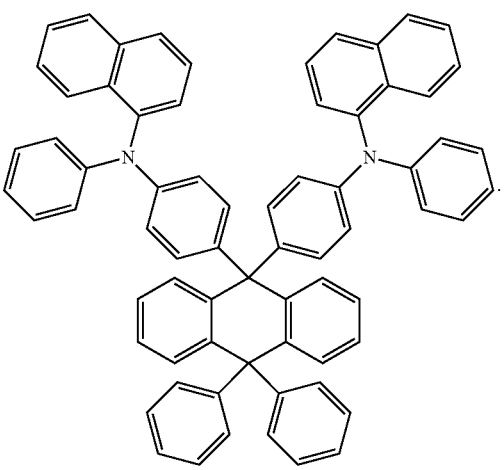
* * * * *